United States Patent [19]

Lamb

[11] Patent Number: 5,025,783
[45] Date of Patent: * Jun. 25, 1991

[54] METHOD OF APPLYING A MEDICAL DRESSING DEVICE

[75] Inventor: Patrick J. Lamb, Indian Mills, N.J.

[73] Assignee: Sparta Surgical Corp., Hayward, Calif.

[*] Notice: The portion of the term of this patent subsequent to Mar. 15, 2005 has been disclaimed.

[21] Appl. No.: 160,202

[22] Filed: Feb. 25, 1988

Related U.S. Application Data

[63] Continuation of Ser. No. 22,863, Mar. 6, 1987, which is a continuation of Ser. No. 902,667, Sep. 2, 1986, abandoned.

[51] Int. Cl.$^5$ .................. A61F 13/00; A61F 15/00
[52] U.S. Cl. ........................... 128/156; 128/155; 604/304; 428/317.1
[58] Field of Search ............... 128/155, 156; 604/304, 604/307, 366, 389; 428/314.8, 317.1, 318.4

[56] References Cited

U.S. PATENT DOCUMENTS

| | | | |
|---|---|---|---|
| 2,858,830 | 11/1958 | Robins | 604/307 |
| 3,122,140 | 2/1964 | Crowe, Jr. | 128/156 |
| 3,961,629 | 6/1976 | Richter et al. | 604/369 |
| 3,978,855 | 9/1976 | McRae et al. | 604/304 |
| 4,377,159 | 3/1983 | Hansen | 128/155 |
| 4,539,982 | 9/1985 | Bailly | 128/156 |
| 4,730,611 | 3/1988 | Lamb | 128/156 |

Primary Examiner—Randall L. Green
Assistant Examiner—Paul Prebilic
Attorney, Agent, or Firm—Eugene E. Renz, Jr.

[57] ABSTRACT

A method of applying a wound management dressing device. A foamed polyurethane pad of a selected size and having a hydrophilic side for contact with a wound and a hydrophobic side for facing away from the wound is positioned on a porous non-woven fibrous sheet of a larger selected size and having an adhesive on the side contacting the hydrophobic side of said pad so that the device presents the hydrophilic side and the adhesive for use in contact with the wound. A non-sticking removable cover is placed over the adhesive side of the sheet to prevent early exposure of the pad and the adhesive.

1 Claim, 1 Drawing Sheet

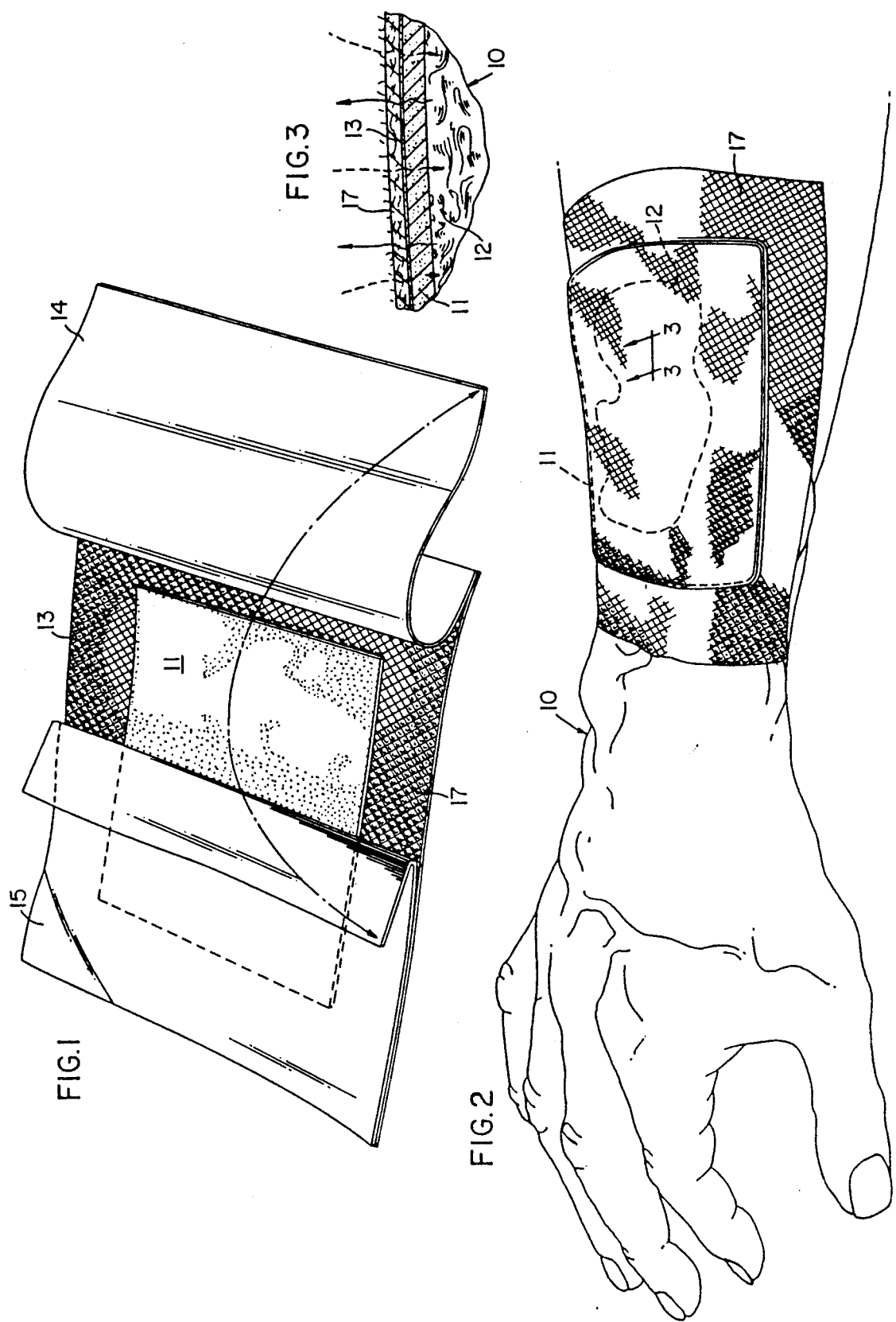

METHOD OF APPLYING A MEDICAL DRESSING DEVICE

This a continuation application of pending Ser. No. 022,863, filed 03/06/87 entitled MEDICAL DRESSING DEVICE, which is a continuation of Ser. No. 902,667, filed 09/02/86 entitled MEDICAL DRESSING DEVICE, now Abandoned.

FIELD OF THE INVENTION

This invention relates to a medical dressing device useful in treating burns, abrasions, lacerations and surgical incisions in which healing of the wound is promoted.

BACKGROUND OF THE INVENTION

Prior art dressings which were applied for wound management have been dressings which ere adapted for wound management rather than designed for such treatment. Normally, standard dressings such as the most common bandages made from gauze and adhesive tape, require changing frequently. One to two days is a long period of time for treating a wound with a single medical dressing or bandage. Accordingly, frequent changing even of inexpensive dressings significantly increases patient cost, both from the large number of bandages required and for the hospital personnel needed to change the dressing.

One form of urethane foam which has been applied as a dressing for various wounds is the Duo-DERM ® dressing, which is a registered trademark of ConvaTec, a Squibb company. This urethane has an acrylic adhesive coating and negative reactions have been noted from contact of wounds with the adhesive. Additionally, the adhesive may tend to mascerate the wound. Johnson & Johnson's Ulcer Dressing also has been proposed for various wounds, but it, too, has an adhesive facing which interferes with the healing process.

What has not been available until the present time is a wound dressing material designed specifically for wound management. This dressing should be suitable for a wide range of wounds including burns, abrasions, lacerations, pressure sores, leg ulcers and both skin graft donor and recipient sites.

An ideal wound management dressing is one which is non-adherent, permeable to water vapor, carbon dioxide and oxygen. The dressing should also be capable of creating a micro-environment which the wounds moist and near the physiologic temperature.

SUMMARY OF THE INVENTION

It has now been discovered that a superior wound management dressing may be prepared and wounds treated using the wound management dressing device to achieve significant improvement in the quality and rate of healing in most, if not all, categories of wounds. Specifically, a wound management dressing device has been discovered which includes a polyurethane foamed pad of a selected size and having a hydrophilic side for contact with the patient and a hydrophobic side for facing away from the patient. Also included is a porous non-woven, fibrous sheet of a larger selected size, having an adhesive on one side. The adhesive side is positioned against the hydrophobic side of the pad so as to present the hydrophilic side and the adhesive for contact with a patient. The selected size is, of course, appropriate to present the pad to the wound and to prevent contact of the adhesive with the wound being treated. Finally, a non-sticking removable cover may be placed over the adhesive side of the sheet, the cover being removable to expose the pad and the adhesive upon use.

Also contemplated in this invention is a method of treating wounds such as burns, abrasions, lacerations and surgical incisions. The method includes the steps of cleaning the wound, applying a wound management dresssing of the type described herein and maintaining the dressing in contact with the wound for up to five to seven days.

Preferred urethane foam pads range in thickness from 0.50 to 1.50 mm. The porous, non-woven fibrous sheet is formed from non-woven fibers, and preferred fibers are polyester fibers. Kendall Corporation manufactures a polyester monomer material under the trademark NOVENETTE ®. Normal permeability of the fibrous sheet is at least 173 cc/hr.

In order to promote healing and reduce pain, it is desirable that the wound management dressing device be sterilized. The pad may be sterilized by irradiation, such as by using cobalt 60.

A non-sticking removable cover may be placed over the adhesive side of the sheet to prevent premature exposure of the pad and the adhesive. A conventional plow design non-sticking cover may be employed.

BRIEF DESCRIPTION OF THE DRAWINGS

These and other objects of the present invention and the various features and details of the operation and construction thereof are hereinafter more fully set forth with reference to the accompanying drawings, wherein:

FIG. 1 is a schematic view showing a preferred embodiment of the present invention prior to application on a wound;

FIG. 2 is a schematic drawing showing the application of the wound management dressing device on a wound for treatment; and FIG. 3 is an enlarged view of a portion of the covered wound shown in FIG. 2, taken at line 3—3.

DETAILED DESCRIPTION OF THE PREFERRED EMBODIMENT

As shown in FIG. 1, the wound management dressing device of this invention is pictured in a partially opened position ready for application, after having been taken out of any sterile packaging which might be needed to maintain the dressing device in a ready-to-use sterile condition. A polyurethane foam pad 11 of a selected size is shown having a hydrophlic side on the top for contacting with the patient. A hydrophobic side is in the reverse side facing away from the reference numeral on the drawing. The hydrophobic side of the polyurethane foamed pad 11 is in contact with a porous non-woven fibrous sheet 13 of a larger selected size. The sheet 13 is designed to be larger than the pad 11 and is particularly required to be porous. A non-sticking removable cover 14 and 15 is placed over the sheet. This design shown in FIG. 1 is the conventional plow of a two-piece, non-sticking removable cover which is designed to be easily removed by pulling the tab portion of the side 14 and curling away the other portion 15 of the cover. An adhesive 117 is placed on the entire side of the sheet 13, holding the foam 11 in place as well as fastening the covers 14 and 15 into place. Because of the non-sticking feature of the covers 14 and 15, they are easily removed from the adhesive.

As is indicated above, the primary functioning element is a polyurethane foamed pad which has a hydrophilic side of contact with the patient and a hydrophobic side for facing away from the patient. The pad is non-adherent and is permeable to water vapor, carbon dioxide and oxygen. It creates a micro-environment which keeps the wound moist and near the physiologic temperature. The foam has been sterilized and is preferably sterilized by irradiation, such as by the use of cobalt 60 irradiation which not only sterilizes the foam pad, but also alters the color, darkening it to a closer to skin color. This foam pad is ideal for a wide range of wounds including burns, abrasions, lacerations, pressure sores, leg ulcers and both skin graft donor and recipient sites.

The pad 11 is supported on a porous, non-woven fibrous sheet 13 sized to permit application of the pad to the wound and having an adhesive 17 on the side bonding the pad to the sheet. The particular sheet employed should have a permeability of at least 175 cc/hr, and preferably between 150 cc/hr and 200 cc/hr. The sheet is formed from non-woven, fibers which are inert to the body, preferably from polyester non-woven fibers. NOVENETTE ® brand polyester fibers manufactured by the Kendall Corporation are preferred. The adhesive 17 which is employed may be any of the conventional acrylic adhesives which are inert at least to undamaged skin. Other conventional pharmaceutical adhesives may also be used.

As shown in FIG. 2, the pad 11 and sheet 13 are in place on a patient's arm 10 which has a severe wound. The wound may be any of a wide range of wounds, including burns, abrasions, pressure sores, leg ulcers and both skin graft donor and recipient sites. An enlarged portion of FIG. 2 is shown in FIG. 3 where the wound 12 is covered by the foam pad 11 and is held in place by a sheet 13. Because the foam pad 11 is hydrophilic on the side adjacent the wound 12, exudate will flow in the direction of the solid arrows from the wound through the foam into the porous sheet 13. Oxygen can reach the wound D, as shown by the dash-line arrows, to aid in healing. The pad 11 thus acts as a thermo-insulator, offering protection against secondary infection, and maintaining an environment which allows for prompt healing. The physiologic temperature is maintained by the pad, which increases cell division, optimizes phagocytosis, and prevents eschar formation. This generates faster and less painful healing.

Products of the present invention as described herein have been tested in comparison with standard bandage treatments, with results showing a significant improvement in the quality and rate of healing in all categories of wounds.

Surpisingly, pain is also significantly reduced, as the nerve endings are covered.

A study was performed of two hundred patients which were treated at an emergency department in a hospital. Eighty patients had partial thickness burns. Seventy patients had deep abrasions. Fifty patients had lacerations. Half of each of the sub-groups were treated with standard therapy as controls. The other half were treated with the present invention.

All the patients treated with the wound management dressing device of this invention showed statistically significant faster healing. The wounds looked different because of the removal of the exudate so that the underlying skin once the exudate has been removed, such as with warm saline solution, reveals a beautifully healing epithelium underneath. Scarring was significantly reduced.

The dresssing of the present invention requires changing only once every five to seven days as opposed to every one to two days with many standard dressings. Accordingly, there is better patient compliance, more convenience for the staff and reduced cost. All of these benefits are of great value.

In using the wound management dressing device of the present invention, the following dressing technique is recommended. The wound is first cleansed and it is valuable to lightly debride loose eschar and necrotic tissue. The dressing size is selected to allow at least a 2 cm overlap at the wound edge in order to avoid leakage of exudate and loss of wound environment. The dressing may be trimmed as desired.

It is advisable to cleanse the wound with a warm isotonic (0.9%) saline solution. Strong antiseptics have been known to cause cell necrosis and should be avoided. The outer non-sticking removable cover is removed and the hydrophilic side facing up from the pad is placed in contact with the wound, ensuring at least 2 cm overlap at the wound edge. It is desirable to avoid excess overlap as exudate may irritate healthy skin. A slight tension is applied to eliminate air pockets and to provide an intimate wrinkle-free contact with the wound surface. The overlying porous, non-woven fibrous sheet is then pressed onto the non-wounded portion of the patient's skin to adhere the product to the patient.

The wound dressing may remain in place for five to seven days, ending upon the amount of exudate which is present. At changing, the dressing may be removed in the traditional manner. Typically, there is no adherence between the wound and the dressing.

While a particular embodiment of the invention has been illustrated and described herein, it is not intended to limit the invention and changes and modifications may be made therein within the scope of the following claims.

What is claimed is:

1. A method of treating wounds such as burns, abrasions, lacerations and surgical incision, comprising the steps of:

cleaning said wound; applying to said wound a foam pad consisting essentially of polyurethane having a thickness ranging from 0.50 to 15.0 mm and sized to cover said wound and extending at least two cm beyond the wound edge, said pad having a hydrophilic side in contact with said wound, and a porous, non-woven fibrous sheet having a permeability to water vapor, carbon dioxide and oxygen of at least 175 cc/hour and sized larger than said pad size and having an adhesive side in contact with the pad, said sheet then being pressed on to the non-wounded portion of the patient's skin to adhere the product to the patient; and maintaining said pad in contact with said wound for five to seven days.

* * * * *